United States Patent [19]

Petersen et al.

[11] Patent Number: 5,565,205
[45] Date of Patent: Oct. 15, 1996

[54] INACTIVATED *MYCOPLASMA HYPOPNEUMONIAE* BACTERIN AND METHOD OF USE THEREOF

[75] Inventors: Gary R. Petersen, Lakeville, Minn.; K. I. Dayalu, Lincoln, Nebr.

[73] Assignee: Solvay Animal Health, Inc., Mendota Heights, Minn.

[21] Appl. No.: 568,427

[22] Filed: Aug. 16, 1990

(Under 37 CFR 1.47)

[51] Int. Cl.$^6$ .................................................. A61K 39/00
[52] U.S. Cl. ............................... 424/264.1; 424/825
[58] Field of Search ...................... 424/92, 88, 89, 424/264.1, 825; 530/403, 413, 416, 820; 435/240.1, 243, 252.1

[56] References Cited

U.S. PATENT DOCUMENTS 4,894,332  1/1990  Schaller et al. .
4,981,684  1/1991  MacKenzei et al. .
4,985,243  1/1991  Faulds et al. .

OTHER PUBLICATIONS

Ross et al. *Am. J. Vet. Res.* vol. 45, No. 10, pp. 1899–1905, 1984.
Goodwin et al, *A. Hyg. Cmb.* vol. 67, pp. 465–475, 1969.
Durišić et al, *Acta Vet (Beograd)*, vol. 25, No. (4), pp. 189–194, 1975.
Vansickle (1991) National Hog Farmer, "Mycoplasma vaccines" issued Nov. 15, 1991.
Quinlan (1990) Large Animal Veterinarian *"Mycoplasma hyopneumoniae*: The MIRD complex" issued Nov./Dec. 1990.
Suvaxyn®/RespiFend™MH advertisement sheet "Impressive results on any scale" Solvay Mycoplasma bacterin field studies data of Spring–Summer 90.
Suvaxyn® description.
"Mycoplasma Induced Respiratory Disease—A closer look at a costly disease complex facing today's swine producers."

*Primary Examiner*—Kay K. A. Kim
*Attorney, Agent, or Firm*—John P. White

[57] ABSTRACT

This invention provides a bacterin comprising a virulent *Mycoplasma hyopneumoniae* isolate, inactivated with binary ethyleneimine, in an amount effective to immunize a swine against infection by *Mycoplasma hyopneumoniae* and a suitable physiologically acceptable carrier. The invention also provides a method of producing this bacterin. The invention further provides a method of inactivating a virulent strain of *Mycoplasma hyopneumoniae* by contacting the *Mycoplasma hyopneumoniae* with binary ethyleneimine. Finally, the invention also provides a method of immunizing swine against infection by *Mycoplasma hyopneumoniae* comprising administering to the swine a dose of the bacterin so as to immunize the swine.

7 Claims, 2 Drawing Sheets

INACTIVATED *MYCOPLASMA HYPOPNEUMONIAE* BACTERIN AND METHOD OF USE THEREOF

BACKGROUND OF THE INVENTION

*Mycoplasma hyopneumoniae* is a ubiquitous swine respiratory pathogen. It infects the respiratory tract of swine, colonizing the trachea, bronchi, and bronchioles. The mycoplasma produces a ciliostatic factor which causes the cilia lining the respiratory passages to stop beating. Eventually, the cilia degenerate, leaving the pig prone to infection by more serious secondary pathogens. The disease caused by *Mycoplasma hyopneumoniae*, enzootic pneumonia, is a chronic non-fatal disease which affects swine of all ages (R. F. Ross, Mycoplasmal diseases, pp. 436–444, in A. D. Laman, et al., (eds.) Diseases of Swine, Iowa State University Press, 1986). Infected pigs show only mild symptoms of cough and fever. However, the economic impact of the disease is significant. The disease is believed to be one of the most important causes of disease-associated loss in swine (Whittlestone, pp. 133–176, in Tully and Whitcomb (eds.), The Mycoplasma Vol 2: Human and Animal Mycoplasmas, New York, Academic Press, (1979)). The disease generally results in inefficient weight gainers, and in stunted and sickly animals. Also, affected swine are often prone to secondary infection by opportunistic organisms (Burch, Pig America pp. 26–27, December, 1982).

There have been numerous attempts to provide a vaccine for protecting swine against mycoplasmal pneumonia. However, such vaccines have not been successful, and the disease remains widespread.

Several investigators have disclosed vaccines comprising recombinantly produced surface antigens of *Mycoplasma hyopneumoniae*, Schaller et al., U.S. Pat. No. 4,894,332, issued Jan. 16, 1990; European Patent Publication No. 283,840, published Sep. 28, 1988.

PCT Publication No. WO 86/00019, published Jan. 3, 1986, discloses a *Mycoplasma hyopneumoniae* vaccine comprising exclusively *Mycoplasma hyopneumoniae* plasma membranes, free of other cell components.

Etheridge et al., *Res. Vet. Sci.* 33: 188 (1982), found incomplete protection against lung colonization by *Mycoplasma hyopneumoniae* when a live vaccine was given intravenously, subcutaneously, or intraperitoneally.

Kristensen et al., *Am. J. Vet. Res.* 42:784 (1981), found no protection of swine against mycoplasmal pneumonia after injection with heat-inactivated *Mycoplasma hyopneumoniae*.

Ross et al., *Am. J. Vet. Res* 45:1899 (1984), found that use of *Mycoplasma hyopneumoniae* extracts prepared by a freeze-thaw procedure to immunize swine, provided only variable protection, and in some instances, enhanced lesion development was noted in immunized swine. These investigators also studied a whole-cell vaccine prepared by formalin inactivation. Formalin inactivation significantly hindered the protective immunogenicity of *Mycoplasma hyopneumoniae*, and this vaccine was not effective.

Yoshioka et al., U.S. Pat. No. 3,917,819, issued Nov. 4, 1975, discloses several killed Mycoplasma vaccines comprising Mycoplasma inactivated with formalin, including an inactivated vaccine for *Mycoplasma hyopneumoniae*. However, this vaccine was prepared by formalin inactivation.

Thus, prior studies with inactivated *Mycoplasma hyopneumoniae* vaccines have been unsuccessful, presumably because the conditions employed, i.e., heat treatment, formalin treatment, or freeze-thawing, destroyed the protective antigenicity potential of the organism.

Accordingly, an effective whole cell vaccine for protecting swine against mycoplasmal pneumonia comprising inactivated virulent *Mycoplasma hyopneumoniae* has not been developed heretofore.

This invention provides a whole-cell *Mycoplasma hyopneumoniae* vaccine or bacteria comprising *Mycoplasma hyopneumoniae* inactivated by treatment with binary ethyleneimine. In contrast with other techniques of inactivation, this method unexpectedly does not adversely affect the protective immunogenicity of the organism such that it may be formulated as an effective bacterin.

SUMMARY OF THE INVENTION

This invention provides a bacterin comprising a virulent *Mycoplasma hyopneumoniae* isolate, inactivated with binary ethyleneimine, in an amount effective to immunize a swine against infection by *Mycoplasma hyopneumoniae*, and a suitable physiologically acceptable carrier.

This invention also provides a method of producing a bacterin which comprises growing a virulent isolate of *Mycoplasma hyopneumoniae* in culture on a suitable medium; treating the virulent *Mycoplasma hyopneumoniae* so grown with binary ethyleneimine so as to inactivate the *Mycoplasma hyopneumoniae*; concentrating the resulting, inactivated *Mycoplasma hyopneumoniae*; recovering the resulting concentrated, inactivated *Mycoplasma hyopneumoniae*; and admixing the concentrated, inactivated *Mycoplasma hyopneumoniae* so recovered with a suitable physiologically acceptable carrier so as to formulate the bacterin.

This invention also provides a method of inactivating a virulent strain of *Mycoplasma hyopneumoniae* which comprises contacting a culture of *Mycoplasma hyopneumoniae* with binary ethyleneimine at a concentration of about 4 mM; incubating the culture under conditions effective to inactivate the *Mycoplasma hyopneumoniae*; and neutralizing the binary ethyleneimine in the culture by the addition of sodium thiosulfate at an effective neutralizing concentration.

This invention also provides a method of immunizing a swine against infection by *Mycoplasma hyopneumoniae* comprising administering to the swine a dose of a bacterin in accordance with the invention so as to immunize the swine against *Mycoplasma hyopneumoniae* infection.

DETAILED DESCRIPTION OF THE INVENTION

Figure 1:
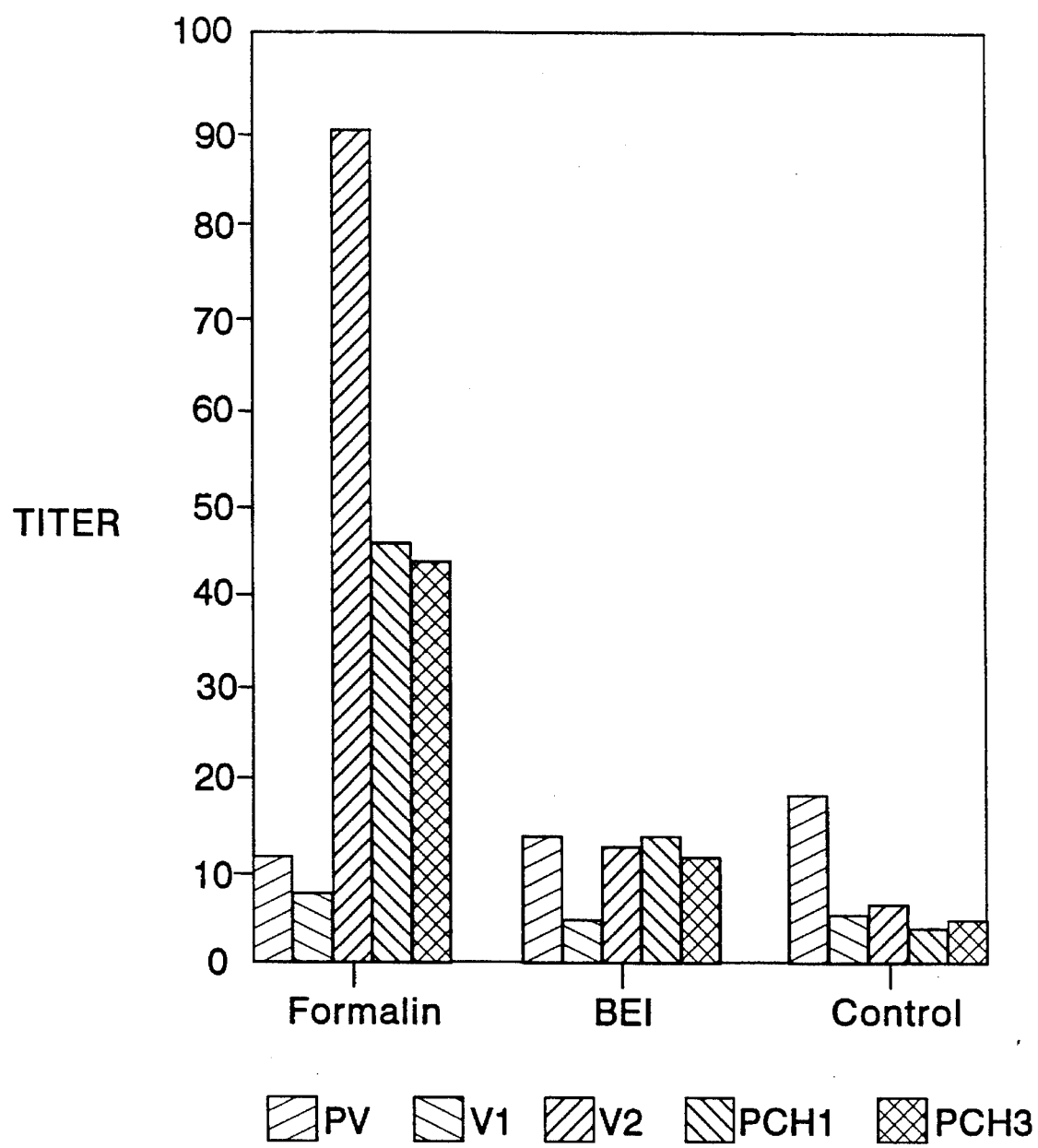
FIG. 1. ELISA results comparing the relative antibody titers induced in pigs by a bacterin made by inactivation of *Mycoplasma hyopneumoniae* with binary ethyleneimine as compared with a bacterin made by inactivation with formalin.
Figure 2:
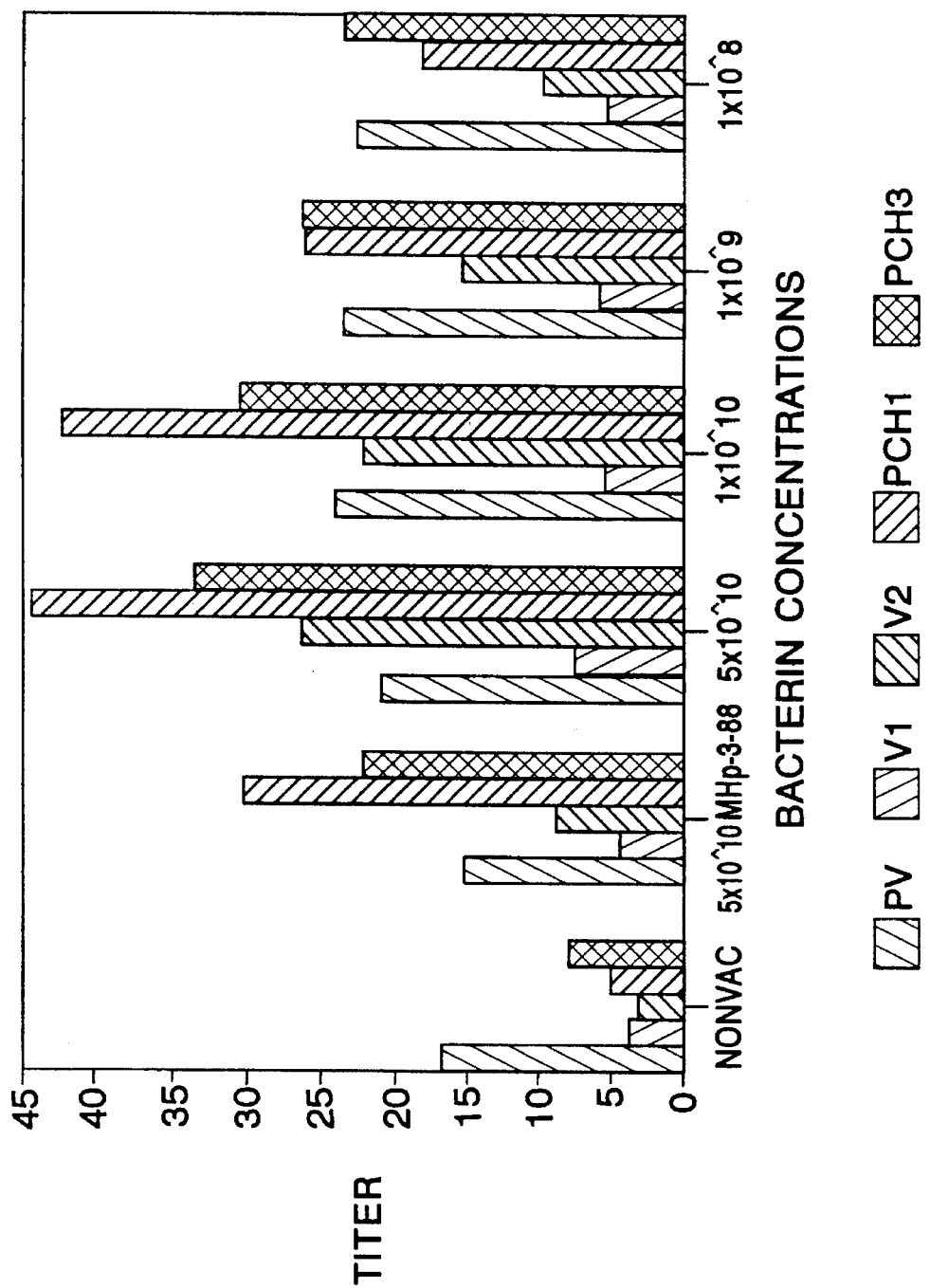
FIG. 2. Results of a minimum protective dose study of the binary ethyleneimine-inactivated bacterin. Serum samples were obtained from each pig in the test at 1 (PV), 3 (V1), 4 (V2), 5 (PCH1) and 7 (PCH3) weeks of age, and antibody titers were assayed by ELISA.

This invention provides a bacterin comprising a virulent *Mycoplasma hyopneumoniae* isolate, inactivated with binary ethyleneimine, in an amount effective to immunize a swine against infection by *Mycoplasma hyopneumoniae* and a suitable physiologically acceptable carrier. In a presently preferred embodiment of this invention, the *Mycoplasma hyopneumoniae* isolate of the bacterin comprises the isolate designated 1002 (ATCC Accession No. 55088).

Although the present invention is described hereinafter with reference to the *Mycoplasma hyopneumoniae* isolate designated 1002 (ATCC Accession No. 55088), it is contemplated that any virulent *Mycoplasma hyopneumoniae* isolate, inactivated with binary ethyleneimine, may be formulated into an effective bacterin. Numerous virulent *Mycoplasma hyopneumoniae* isolates are known in the art and are available from various sources including the American Type Culture Collection. Finally, the deposit of the 1002 isolate was made pursuant to, and in satisfaction of, the Budapest Treaty on the International Recognition of the Deposit of Microorganisms for the Purpose of Patent Procedure, with the American Type Culture Collection, 12301 Parklawn Drive, Rockville, Md. 20852 on Aug. 14, 1990.

The bacterin further comprises a suitable physiologically acceptable carrier. A wide variety of such carrier are well known in the art, and the selection of a specific carrier is well within the level of those skilled in the art. Merely by way of example, suitable physiologically acceptable carriers include distilled or deionized water, saline, or mineral oil.

In a presently preferred embodiment, the bacterin further comprises an effective amount of an adjuvant. An "adjuvant," as used herein, is a potentiator of the immune response. Adjuvants may comprise poisons, irritants, and in general substances which boost the immune response of the injected animal. In a presently preferred embodiment of the invention, the adjuvant comprises a polymer of acrylic acid, e.g., a homopolymer. One commercially available example of such a homopolymer of acrylic acid is Carbopol 941 (B. F. Goodrich Co., Cleveland, Ohio). The chemical formula for Carbopol is $(CH_2CHOOOH)_n$. Effective amounts of any specific adjuvant may be readily determined so as to optimize the potentiation effect of the adjuvant on the immune response of an animal vaccinated with the bacterin. In general, an effective amount of acrylic acid polymer useful as an adjutant is about 0.2% (w/v) of the bacterin.

The bacterin of the invention comprises the virulent *Mycoplasma hyopneumoniae* isolate, inactivated with binary ethyleneimine, in an amount effective to immunize a swine. To "effectively immunize" a swine against infection by *Mycoplasma hyopneumoniae* means that the bacterin prevents or reduces the severity of mycoplasmal pneumonia. In any event, those skilled in the art are able to readily determine for any specific isolate and carrier combination, with and without an adjuvant being present, the amount of *Mycoplasma hyopneumoniae*, inactivated with binary ethyleneimine, effective to immunize a swine. In the presently preferred embodiment of the invention, the effective amount is at least about $10^9$ *Mycoplasma hyopneumoniae* DNA cell equivalents per milliliter of bacterin. (See Methods and Materials, hereinafter, for a discussion of "DNA cell equivalents".)

This invention also provides a method of producing a bacterin which comprises growing a virulent isolate of *Mycoplasma hyopneumoniae* in culture on a suitable medium; treating the virulent *Mycoplasma hyopneumoniae* so grown with binary ethyleneimine so as to inactivate the *Mycoplasma hyopneumoniae*; concentrating the resulting, inactivated *Mycoplasma hyopneumoniae*; recovering the resulting concentrated, inactivated *Mycoplasma hyopneumoniae*; and admixing the concentrated, inactivated *Mycoplasma hyopneumoniae* so recovered with a suitable physiologically acceptable carrier so as to formulate the bacterin. In a preferred embodiment of the invention, the *Mycoplasma hyopneumoniae* isolate designated 1002 (ATCC Accession No. 55088) is used in formulating the bacterin.

More specifically, a virulent isolate of *Mycoplasma hyopneumoniae* is grown in culture in a suitable medium containing Mycoplasma broth base, yeast extract, glucose, L-cysteine, ampicillin, thallium acetate, swine serum and deionized water. One such medium which is presently preferred is described in greater detail hereinafter.

The precise conditions under which the isolate is grown may vary depending upon the precise composition of the medium and the specific isolate being grown. However, the isolate is typically grown from about 48 hours to about 144 hours, measured from the time of incubation to the time of harvest. The virulent *Mycoplasma hyopneumoniae* isolate so grown is then treated with binary ethyleneimine so as to inactivate the *Mycoplasma hyopneumoniae*. Thus, the culture of the isolate may be contacted with binary ethyleneimine at a concentration of about 1 to about 10 mM, e.g., about 4 mM. The culture is then incubated under conditions effective to inactivate the *Mycoplasma hyopneumoniae*, e.g., for at least about 12 hours at about 37° C. The binary ethyleneimine in the culture is then neutralized by adding sodium thiosulfate at an effective neutralizing concentration, e.g., a concentration from about 10 mM to about 20 mM, such as about 16 mM.

In one embodiment of the invention, the binary ethyleneimine which is used to contact and inactivate the *Mycoplasma hyopneumoniae* is formed in situ by adding L-bromoethylamine hydrobromide to the culture in an amount, which upon conversion to binary ethyleneimine, results in formation of the desired inactivating concentration, e.g. about 4 mM.

The resulting, inactivated *Mycoplasma hyopneumoniae* is then concentrated. Various methods are known in the art for concentrating such organisms. For example, the organisms may be concentrated by centrifugation, e.g., ultracentrifugation, or by filtration, e.g., ultrafiltration.

The concentrated, inactivated *Mycoplasma hyopneumoniae* which result are then recovered, again using methods well known in the art. Finally, the resulting concentrated, inactivated *Mycoplasma hyopneumoniae* so recovered is admixed with a suitable physiologically acceptable carrier so as to formulate the bacterin. Optimally, the admixture may further comprise an effective amount of EDTA, e.g., about 0.05% to about 0.20%, particularly at least about 0.07% (w/v) of the bacterin, or an effective concentration of thimerosol, e.g., about 0.005% to about 0.05%, particularly about 0.01% (w/v) of the bacterin.

The bacterin may also be produced by any of several modifications of the preceding method. For example, the *Mycoplasma hyopneumoniae* may be concentrated before inactivation, rather than after. Also, preparation of the bacterin may be carried out by repeating the inactivation step both before and after the concentrating step.

The concentrated, binary ethyleneimine-inactivated *Mycoplasma hyopneumoniae* is thus formulated as a bacterin by adding a suitable carrier. A diluent, dye, or preservatives may also be added. A chelator such as EDTA may be added, preferably to a final concentration of at least about 0.07% (w/v). Diluents such as saline, or other carriers well known in the art, may be used to dilute the inactivated *Mycoplasma hyopneumoniae* in formulating the bacterin. Preservatives may also be added. In one embodiment of the invention, thimerosal is added as the preservative, to a final concentration of at least about 0.01% (w/v).

This invention also provides a method of inactivating a virulent strain of *Mycoplasma hyopneumoniae* which comprises contacting a culture of *Mycoplasma hyopneumoniae* with binary ethyleneimine at a concentration of about 4 mM; incubating the culture under conditions effective to inactivate the *Mycoplasma hyopneumoniae*, such as, for an effective time, e.g. about 12 hours, at an effective temperature, e.g. about 37° C.; and neutralizing the binary ethyleneimine in the culture by the addition of sodium thiosulfate to the culture at an effective neutralizing concentration, e.g. about four times the concentration of binary ethyleneimine, i.e., about 16 mM if the binary ethyleneimine concentration is about 4 mM. Also, as indicated hereinabove, the binary ethyleneimine may be formed in situ by adding L-bromoethylamine hydrobromide to the culture.

This invention also provides a method of immunizing a swine against infection by *Mycoplasma hyopneumoniae* comprising administering to the swine at least one dose of the bacterin so as to immunize the swine against *Mycoplasma hyopneumoniae* infection. The bacterin may, in principle, be administered through various routes. However, in the presently preferred embodiment of the invention, the bacterin is administered intramuscularly. Moreover, it is presently preferred that the bacterin dose comprise about 2 ml of the bacterin, each ml containing about $10^9$ *Mycoplasma hyopneumoniae* DNA cell equivalents. The bacterin is desirably administered twice to the swine; once at about one week, and once at about three weeks, after the birth of the swine.

A bacterin in accordance with the present invention, intended for administration by injection, comprises inactivated, virulent *Mycoplasma hyopneumoniae* suspended in an inert physiologically acceptable liquid diluent. Suitable diluents include water, saline, or any of many other diluents well known in the art. Advantageously, the *Mycoplasma hyopneumoniae* are suspended in a sterile diluent under aseptic conditions.

The bacterin intended for injection may be rendered isotonic by any conventional technique, for example, by dialysis against a salt solution that is isotonic with the blood of swine. Any salt solution suitable for use as an injection medium may be used to render the bacterin isotonic.

Further, the bacterin may be prepared either as a concentrated composition for dilution prior to use or as a composition ready for use. In the latter case, the concentration of the inactivated, virulent *Mycoplasma hyopneumoniae* is at least about $10^9$ DNA cell equivalents per milliliter.

The binary ethyleneimine-inactivated *Mycoplasma hyopneumoniae* of the present invention may also be used as a component of a vaccine containing one or more other active ingredients, i.e., antigenic substances capable of inducing a protective immune response against *Mycoplasma hyopneumoniae* or against other disease-causing agents.

Materials and Methods

The microorganism used in the preparation of the bacterin is the virulent *Mycoplasma hyopneumoniae* isolate designated 1002 and deposited under ATCC Accession No. 55088. This strain, originally isolated from an infected lung by culturing a $10^{-2}$ dilution of lung homogenate in Mycoplasma broth, was passed in broth seven times to establish the Master Seed ("X").

The identity of the Master Seed ("X") was established by plating on Mycoplasma Broth Agar and examining the growth for typical *Mycoplasma hyopneumoniae* morphology. *Mycoplasma hyopneumoniae*, Strain J, obtained from NVSL, was used as a reference for comparison. The identity of the Master Seed ("X") was further established by SDS-PAGE and immunoblot comparison with References *Mycoplasma hyopneumoniae*, Strain J, and other related Mycoplasma species.

The Master Seed ("X") is the seventh passage of the isolate designated as 1002. The production seed is the "X+2" passage. Seed cultures range from "X+3" to "X+6". Production cultures range from "X+6" to "X+7".

The seed and production cultures are propagated in the following medium:

1. Mycoplasma Broth Base (Commercial) . . . 16.800 grams
2. Yeast Extract (Commercial) . . . 1.000 grams
3. Glucose . . . 5.000 grams
4. L-Cysteine Hydrochloride . . . 0.100 grams
5. Ampicillin . . . 0.250 grams
6. Thallium Acetate, U.S.P . . . 0.250 grams
7. Phenol Red (Indicator Dye) [for use in Seed Medium] . . . 0.020 grams
8. Normal Sterile Swine Serum (May be Heat-Inactivated at 58.5° C. for 30 minutes prior to use for Seed Medium) . . . 100.000 ml
9. Deionized Water . . . q.s. . . . 1,000,000 ml When the ingredients are thoroughly dissolved, the pH is adjusted to 7.8±0.4 with NaOH. The solution is sterilized by filtration through either a sterile 0.3-micron depth filter, a sterile 0.3-micron membrane filter, or a sterile 0.2-micron cartridge filter into sterile containers. The depth, membrane, or cartridge filters and holders are sterilized for no less than 30 minutes at 121° C.±2° C. prior to use.

The base medium may be autoclaved without the glucose, L-cysteine hydrochloride, ampicillin, and swine serum for a minimum of 30 minutes at 121° C.±2° C. prior to use. The L-cysteine hydrochloride and ampicillin are sterilized by filtration through a 0.2-micron filter, and are aseptically added to the base medium.

The glucose solution is autoclaved separately as a 30% (w/v) solution at 121° C.±2° C. for 30 minutes. Normal sterile swine serum is added aseptically. The pH of the complete medium is adjusted to 7.8±0.4 using sterile 5N NaOH. The seed culture medium may be stored at 2° C. to 7° C. for up to 30 days, and the autoclaved production culture may be stored at 2° C. to 7° C. for up to 10 days.

Seed cultures are grown in 250- to 4,000-ml polycarbonate or glass flasks, 12-liter glass jugs, 28- and 200-liter fermentation vessels containing 30% to 80% medium. Production cultures are grown in 200- to 3,000-liter fermentation vessels containing 30% to 80% medium. The master seed ("X") is maintained in 100% medium at −20° C. or colder. The production seed ("X+2") is maintained in 90% medium and 10% glycerol at −20° C. or colder.

Suspensions are prepared for seeding or inoculation by rapidly thawing frozen seed cultures ("X" or "X+2") and inoculating into medium at a rate of 5% to 15% (v/v). Seed cultures are serially transferred into medium at a rate of 5% to 15% (v/v).

Seed and production mediums are inoculated by the following technique. The frozen production seed culture ("X+2") is used to inoculate medium in 250-ml flasks at a rate of 5% to 15% (v/v) to produce the "X+3" passage. Subsequent seed cultures ("X+4" through "X+9") are produced as the result of serially transferring at a rate of 5% to 15% (v/v) into the appropriate containers. 250-ml Flask cultures may be used to inoculate 4,000-ml flasks at a rate of 5% to 15% (v/v). 4,000-ml Flask cultures may be used to inoculate 12-liter jugs at a rate of 5% to 15% (v/v). 12-liter Jug cultures may be used to inoculate 28- to 200-liter fermentation vessels at a rate of 5% to 15% (v/v). 28- to 200-liter fermentation vessel cultures may be used to inoculate production fermentation vessels ranging from 200 to 3,000 liters at a rate of 5% to 15% (v/v). Seed cultures and production cultures are incubated at 37° C.±2° C. for 48 to 120 hours. All cultures are incubated with agitation throughout the growing period. Fermentation vessels may be aerated by the infusion of sterile air. The pH of the seed and production cultures may be maintained at 7.4±0.4 by the addition of a sterile NaOH solution. A sterile solution of 30% glucose may be added to the production culture as needed.

The character of growth is determined by macroscopic examination. Characteristic growth is indicated by a decrease in the pH of the medium (seed culture) or increased utilization of NaOH in order to maintain pH of the medium (production cultures).

The amount of growth is determined by DNA fluorometry as follows: four 1.5-ml aliquots of culture are collected in microfuge tubes. The samples are centrifuged at 12,000×g for ten minutes. The supernatants are completely drained off and the pellets re-suspended in 120 μl of: 10 ml Tris (pH 7.4), 150 mM NaCl, 1 mM ethylenediaminetetraacetic acid (EDTA), and 1% (w/v) sodium dodecyl sulfate (TNES). The re-suspended pellets are vigorously vortexed for ten seconds. Ten μl of the re-suspension pellets is mixed in a glass cuvette with two ml of Hoechst dye solution: 0.4 μg/ml in 10 mM Tris (pH 7.4), 150 mM NaCL, and 1 mM EDTA (TNE). The cuvette is then placed in a fluorometer which has previously been calibrated using DNA standards. The amount of fluorescence is proportional to the amount of DNA present. The number of *Mycoplasma hyopneumoniae* DNA cell equivalents (MHDCE) in the culture is calculated using the following formula:

$$\frac{MHDCE}{\text{Milliliter of culture}} = \frac{Ng \text{ DNA}}{\text{Test Aliquot}} \times \frac{12 \text{ Test Aliquots}}{\text{Sample}} \div \frac{1.5 \text{ ml culture}}{\text{Sample}} \div \frac{0.8 \times 10^{-6} \text{ ng DNA}}{MHDCE}$$

or $$\frac{MHDCE}{\text{Milliliter of Culture}} = \frac{Ng \text{ of DNA}}{\text{Test Aliquot}} \times 10^7$$

Prior to harvest, production cultures are examined for character and amount of growth and for contamination by macroscopic evaluation.

Prior to inactivation, production cultures are adjusted to a pH of 8.2±0.2 by the addition of sterile 5N NaOH.

For inactivation, L-bromoethylamine hydrobromide (BEA) is added directly to the production culture within the fermentation vessel to a final concentration of no less than 4 mM.

The culture is maintained with agitation at 37° C.±2° C. for 12 to 24 hours.

The mycoplasmas are inactivated by exposure to binary ethyleneimine. The binary ethyleneimine (BEI) (primary inactivating agent) generated in situ during the incubation of L-bromoethylamine hydrobromide (BEA) in the production culture is neutralized by the addition of sodium thiosulfate directly to the inactivated production culture in the fermentation vessel to a final molar concentration of no less than four times the binary ethyleneimine (BEI) molar concentration.

The culture is maintained with agitation at 37° C.±2° C. for 12 to 24 hours. The minimum and maximum times from inoculation to harvest are 48 and 144 hours, respectively.

For harvesting, the production vessel materials are pooled into a sterile container. Harvest fluids are concentrated to 10%±5% of the original volume by centrifugation and/or ultrafiltration and may be diafiltered using a sterile saline solution. The concentrate may be re-inactivated by the addition of L-bromoethylamine hydrobromide (BEA) to a final concentration of no less than 4 mM. The concentrate is incubated at 37° C.±2° C., with stirring, for 12 to 24 hours. The binary ethyleneimine (BEI) generated during inactivation is then neutralized by the addition of sodium thiosulfate to a final molar concentration four times the binary ethyleneimine (BEI) molar concentration. The concentrate is incubated at 37° C.±2° C., with stirring, for 12 to 24 hours. Thimerosal and ethylenediaminetetraacetic acid (EDTA) are added to the final concentration of 0.01% and 0.07%, respectively.

Only production cultures exhibiting characteristic growth, are harvested. A gram-stain is prepared from each production container prior to harvest.

The bacterin is preserved by the addition of thimerosal and ethylenediaminetetraacetic acid (EDTA) at no more than 0.01% and 0.07%, respectively.

The bacterin is adjuvanted by the addition of Carbopol (B. F. Goodrich Co.) to a final concentration of 0.2% (w/v).

A sterile saline solution may be used as diluent. Red Dye FD&C 40 may be added to the bacterin to a final concentration of 15 mg per liter.

The concentration of Mycoplasma cells in the final product is no less than $2 \times 10^9$ *Mycoplasma hyopneumoniae* DNA cell equivalent per 2.0-ml dose, as determined by the DNA-fluorometric assay.

Satisfactory Mycoplasma concentrates are aseptically combined with the adjuvant, preservative, dye, and diluent into a sterile container equipped with an agitator and mixed for no less than 30 minutes.

The present invention is further described with respect to the following examples. However, the scope of the invention is not intended to be, and should not be construed to be, limited thereby.

EXAMPLE 1

The virulence of four different strains of *Mycoplasma hyopneumoniae* (Mhp): Mhp 1002-strain, Mhp 1005-NB 12 strain, Mhp 1003-J Strain, Mhp 1004-11 strain, and Mhp 1006-415 strain were evaluated.

The virulence of the strains tested was determined by lesions on the lungs of the challenged pigs. Based upon this criterion, *M. hyopneumoniae* 1002 was determined to be virulent and was chosen for use as the challenge strain and for bacterin preparation.

Twenty nine three-week-old, pseudorabies-tested pigs were divided into four groups of eight, eight, seven and six. The pigs were reared in isolation until 6 weeks of age at which time they were challenged.

A low-passage stock culture of each of the four strains of *Mycoplasma hyopneumoniae* was thawed and a 10% inoculum of each strain was added to Pleuropneumonia-like organism (PPLO) complete medium (see page 51). The cultures were incubated at 37° C. for 12 days.

Six ml of the appropriate challenge culture was administered into each nostril using a 10-ml syringe with a 1½ inch rubber tubing attached. A plastic bag was held over the nostrils for a short period to promote inhalation. This challenge was repeated for three consecutive days.

Quantitation of the challenge inoculum was performed by determining color changing units (CCU).

All the pigs were euthanized and subjected to necropsy three weeks after the first challenge. The lungs were removed and examined for characteristic *M. hyopneumoniae* lesions.

Areas of a lung with typical *M. hyopneumoniae* lesions were cut out and placed in suitable sterile containers and stored frozen at −70° C. Attempts to isolate *M. hyopneumoniae* from these organ samples were made at a later date.

The following results are tabulated in Tables 1 and 2. Four different strains of *M. hyopneumoniae* were used in this study. The total dosage ranged from $9.0\times10^7$ to $9.0\times10^{10}$ CCU/pig. The percentage of animals/group with lung lesions ranged from 17% to 50%. In all pigs, the lung lesions were restricted to the cardiac and apical lobes and were characteristic of *M. hyopneumoniae.*

There appeared to be no correlation between the dosage (CCU/pig) and the extent of lung lesions. *M. hyopneumoniae* 1002 and Mhp 1005-NB12 appeared to be the most virulent. However, *M. hyopneumoniae* 1002 grew faster and to a higher CCU level in our PPLO medium.

The attempts to isolate the challenge strains from collected lung samples were successful. The cultures were observed under a phase-contrast microscope and appeared to be highly suggestive of *M. hyopneumoniae.*

*M. hyopneumoniae* 1002 was the choice for future work based on lung involvement, growth in PPLO medium and prior studies using the isolate.

TABLE 1

Lung Lesion Involvement Resulting From Intranasal Inoculation of Four Different Strains of *Mycoplasma hyopneumoniae*

| *M. hyopneumoniae* strain | Total CCU/Pig | No. Infected/ Total |
|---|---|---|
| 1002 | $9 \times 10^7$ | 4/8 (50%) |
| 1005 - NB12 | $9 \times 10^6$ | 4/8 (50%) |
| 1003 - J | $9 \times 10^{10}$ | 1/6 (17%) |
| 1004 - 11 | $9 \times 10^6$ | 2/7 (29%) |

TABLE 2

Lung Lesion Involvement Produced by Four Different Strains of *M. hyopneumoniae*

| *M. hyopneumoniae* Strain | Observations/ Area of Lung Involved |
|---|---|
| 1002 | |
| 214 | Left cardiac lobe - 85%. Left apical lobe - 10%. Right cardiac lobe - 80%. Accessory lobe - 60%. |
| 217 | No Lesions. |
| 218 | Right apical lobe - particularly ventral surface. Right cardiac anterior - 50%. Left apical ventral surface - patchy. Left cardiac-outer 50%. Dorsal and ventral lesion extended to extreme edge of diaphragmatic lobe. Left diaphragmatic lobe - extreme edge of dorsal and ventral surface. |
| 221 | No Lesions. |
| 224 | No Lesions. |
| 368 | No Lesions. |
| 369 | Both cardiac lobes - ventral surfaces. |
| 370 | Left cardiac lobe - tip 10%. |
| 1005 - NB12 | |
| 132 | Right apical lobe - localized lesions in the border and ventral surface. |
| 133 | Right apical lobe and right cardiac lobe - patchy lesions on ventral surface. Left apical lobe and left cardiac lobe - patchy lesion on ventral surface. |
| 134 | No Lesions. |
| 135 | No Lesions. |
| 136 | No Lesions. |
| 138 | No Lesions. |
| 139 | Right apical lobe - anterior edge - 100%. Right cardiac lobe - patchy lesions on ventral surface. |
| 140 | Right apical lobe - patchy lesions on ventral surface. |
| 1003 - J | |
| 19 | No Lesions. |
| 20 | No Lesions. |
| 21 | Right apical lobe - sparse lesions on anterior edge and external tip - 10%. |
| 25 | No Lesions. |
| 169 | No Lesions. |
| 170 | No Lesions. |
| 1004 -11 | |
| 6 | No Lesions. |
| 7 | No Lesions. |
| 8 | No Lesions. |
| 9 | Right apical lobe - on extreme edge. Left apical lobe - tip 10%. |
| 10 | Right apical lobe on edge. |
| 258 | No Lesions. |
| 337 | No Lesions. |

PPLO Complete Medium

I. Components

A. PPLO broth w/o crystal violet (800 ml)

a. 16.8 g of Difco PPLO w/o crystal violet dissolved in deionized water to equal 800 ml.

b. Mix with 500 g of amberlite IRA 400 on a magnetic stirrer 2 hours at room temperature.

c. Filter out amberlite with paper filter.

B. Thallous Acetate (2.5 ml)

a. 0.25 g of thallous acetate dissolved in total volume of 2.5 ml deionized water.

C. Phenol Red (0.5 ml)

a. 0.02 g phenol red dissolved in 0.5 ml deionized water.

D. L-cysteine hydrochloride (1 ml)

a. 0.1 g 1-cysteine hydrochloride dissolved in 1.0 ml deionized water (make on day of use).

E. Ampicillin (2.5 ml)

a. 0.25 g of ampicillin dissolved in 2.5 ml of deionized water (make on day of use).

F. Glucose (50 ml)

a. 10 g of glucose dissolved in a total volume of 50-ml deionized water.

G. Yeast Extract (50 ml)
   a. 25 g yeast (Fleischman Co.) dissolved in 150-ml deionized water stirring rapidly on a magnetic stirrer.
   b. 0.81 ml 10N NaOH slowly added to the yeast mixture.
   c. Autoclave at 15 psi for 15 min.
   d. Store overnight at 4° C.
   e. Centrifuge 8000 rpm for 30 min.
   f. Pour off, collect and measure supernatant.
   g. Add 2 ml of 1N HCl/100 ml supernatant.
   h. Centrifuge 10,000 rpm for 1 hour.
   i. Pour off and collect supernatant.
   j. Filter supernatant first through a 0.8 micron filter, then a 0.45 micron filter and finally a 0.2 micron filter.
   k. Store at 4° C.

H. Gibco Porcine Serum (100 ml)
   a. Heat activate for 30 minutes at 56° C.

II. Combination of Components
   a. Combine components in amounts listed in parenthesis.
   b. Filter through first a 3.0 micron filter, then a 0.45 micron filter and finally a 0.2 micron filter.
   c. Incubate at 37° C. overnight to check for purity.
   d. Store at 4° C.

Color Changing Units

Materials and Equipment:
MHp complete medium
12—12×75 mm snap-cap plastic tubes
pipette or Cornwall syringe
culture Procedure:
1) Add 1.8 ml of medium to all 12 tubes.
2) Add 0.2 ml of culture to first tube and dilute 10-fold to tube 11. Discard 0.2 ml of culture from tube 11.
3) Tube 12 has no culture, to serve as control.
4) Snap tubes securely and incubate for 14 days at 37° C.
5) Check for color change to determine titer. On day 14, record the highest dilution of which the color has changed from red to yellow and calculate the CCU/ml as follows:

$$\text{CCU/ml} = \text{Highest color change dilution} \times \frac{0.2}{2.0}$$

EXAMPLE 2

Binary ethyleneimine (BEI)-inactivated and formalin-inactivated *Mycoplasma hyopneumoniae* bacterins were evaluated for their ability to protect pigs against a virulent challenge with *M. hyopneumoniae*.

The formalin inactivated bacterin gave significantly higher ELISA titers than the BEI-inactivated bacterin. Only the BEI-inactivated bacterin, however, provided significant protection from challenge. These results suggest that local secretory antibody and/or cellular mediated immunity play a more important role in the immune response to *M. hyopneumoniae* than circulating antibody. Upon evaluation of these results, the BEI-inactivated bacterin will be the choice for future studies.

Pigs used in this study were from Ionia Pigs, Incorporated (Ionia, Iowa).

*Mycoplasma hyopneumoniae* strain 1002, originally designated P-5723-3 (Dr. Charles Armstrong, Purdue University), was successively passed in a medium as described above to passage X+7 using a 10% inoculum for each passage. Each passage was incubated at 37° C. for 72–80 hours swirling at 75 rpm.

At the end of the incubation of the X+7 passage culture the extent of growth and concentration of mycoplasma were evaluated visually by the color of the culture medium and phase contrast microscopy, respectively. A sample was taken to determine the number of organisms present using the quantitation method of color changing units (CCU).

Inactivation—Formalin:

Formalin was added to 400 ml of an X+7 culture to a final concentration of 0.2%. The cell suspension was swirled at 75 rpm for 24 hours at 37° C.

Inactivation—Binary Ethyleneimine (BEI):

To 400 ml of an X+7 culture, 40 ml of 2% (w/v) sodium bicarbonate was added to raise the pH to 7.5. A 0.33 gram amount of 2-bromoethylamine hydrobromide in 10 ml deionized water was sterilized through a 0.2 μm filter and added to the culture. The culture was swirled, in situ, (75 rpm) at 37° C. for 24 hours. Ten ml deionized water containing 0.5 g sodium thiosulfate was filter sterilized and added to the inactivated culture to neutralize the BEI. The neutralized culture was swirled (75 rpm) at 37° C. for 24 hours.

To prepare the bacterins, cells of each inactivated culture were pelleted at 15,000×g for 40 minutes at 4° C. then resuspended in approximately 50 ml PBS and washed in this manner 3 times. The final pellet was resuspended in approximately 50 ml PBS. The resuspended cells were mixed with Carbopol so that the final preparation would contain Carbopol at a concentration of 0.2% (w/v) and a 2-ml dose would deliver $5 \times 10^{10}$ CCU. The vaccines also contained 0.005% (w/v) thimerosal as a preservative.

Piglets approximately one and three weeks of age were vaccinated intramuscularly in the neck region with a 2-ml dose of the appropriate bacterin. One group of pigs was not vaccinated and served as challenge controls.

*M. hyopneumoniae* isolate 1002 X passage was passed to the X+2 level in the medium previously described using a 10% inoculum. The culture was swirled at 75 rpm for 80 hours at 37° C. At the end of the incubation of the X+2 passage, the extent of growth and concentration of Mycoplasma were evaluated in the same manner as the mycoplasma concentration for the vaccine. On the same day that animals received the primary vaccination, several one-week-old pigs were inoculated with 2-ml of the above challenge culture. The inoculum was injected through a 3½ French Tom Cat Catheter inserted through a 15-gauge needle into the trachea. The infection was allowed to proceed for three weeks.

The challenge culture for the test pigs was prepared as described above. However, the X+2 passage culture was used for challenge after 72, 96 and 120 hours of growth. At four weeks of age (1 week following the second vaccination) non-vaccinates and vaccinates were sedated with 1–2 ml of PromAceVetalar (1:10) solution. After sedation, a 3-ml dose of the challenge culture was given intranasally (1.5 ml per nostril) via a syringe connected to a short rubber tube which was inserted in the nostril. This procedure was repeated on the following two days using the same culture. A sample of the 72-hour culture was quantitated for viable Mycoplasma present as determined by CCU. The titer was between $5 \times 10^8$ and 5×10⁹ CCU/ml. At the time of challenge, three to four seeder pigs (infected 3 weeks earlier) were co-mingled with each test group as a natural means of challenge.

Blood samples were taken from all piglets on the day of the first vaccination (PV), the day of the second vaccination (V1), the first day of challenge (V2), one week post-challenge (PCH1), and three weeks post-challenge (PCH2). The serum from each blood sample was heat inactivated at 56° C. for 30 minutes and stored at −20° C. The sera were tested for *M. hyopneumoniae* antibody by ELISA assay.

Twenty-one days after the initial challenge, the animals were euthanized by injection of 2–5 ml of the Euthanasia solution directly into the anterior vena cava. The chest cavity was immediately opened and the lungs removed intact. The lungs were photographed and gross lesions scored as follows. Ten points are allocated to each apical and cardiac lobe, five points to the intermediate lobe and five points to each leading edge of the diaphragmatic lobes, thus, if all these areas were totally consolidated (which would be an unusually severe case), the lesion score would be 55. The actual score obtained is then expressed as a percentage of this maximum score. This is defined as the % lesion score. Diagrams were used for recording lesion scores.

Percent lesion scores were statistically analyzed by a two-tailed Student's T-test in order to identify significant differences between treatment groups.

The ELISA results are presented in FIG. 1. At one week of age, prior to any vaccination (PV), all groups had anti-*M. hyopneumoniae* circulating antibodies. These titers decreased at three weeks of age, prior to revaccination (V1). At 4 weeks of age, prior to challenge (V2), the animals vaccinated with either the formalin- or the BEI-inactivated bacterins had higher titers than the non-vaccinated animals. However, the formalin-inactivated bacterin had elicited dramatically higher titers than the BEI-inactivated bacterin.

The lesion score results are presented in Table 3. The BEI-inactivated bacterin reduced the mean percent lesion score by approximately 60%. This reduction is highly statistically significant ($p<0.01$).

There appeared to be no correlation between the serological response and the percent lesion scores. Whereas the formalin inactivated bacterin elicited the highest circulating antibody titers, only the BEI-inactivated bacterin protected the pigs from challenge.

These results suggest that circulating antibodies do not play a major role in immunoprotection against infection by *Mycoplasma hyopneumoniae*. Local secretory antibody and/or cell-mediated immunity are probably far more important. The BEI-inactivated bacterin appears to properly invoke these arms of the immune system.

TABLE 3

Percent Lesion Scores of Vaccinated Pigs
Challenged With *M. hyopneumoniae* Strain 1002

| Bacterin | Percent Lesion Score X + s.d. |
|---|---|
| Formalin-inactivated | 26.4 + 19.2[a] |
| BEI-inactivated | 11.6 + 6.9[b] |
| Non-vaccinated | 30.4 + 13.7 |

[a]Not significantly different from non-vaccinated ($p > 0.5$) by two-tailed T-test
[b]Significantly different from non-vaccinated ($p < 0.01$) by two-tailed T-test.

EXAMPLE 3

The *Mycoplasma hyopneumoniae* bacterin was evaluated in a duration of immunity study. The bacterin was administered to pigs at 1 and 3 weeks of age. Non-vaccinated litter mates served as controls. A portion of the vaccinates and controls were challenged with virulent *M. hyopneumoniae* at 1 month of age. A second portion of vaccinates and controls were challenged at 2 months of age. The remaining animals were challenged at 4 months of age. Significant ($p<0.05$) protection from challenge was seen in vaccinates at 1, 2 and 4 months of age. These results indicate that vaccination at 1 and 3 weeks of age confers long lasting protection to pigs.

The bacterin used in this study contained 9.0 $\log_{10}$ *Mycoplasma hyopneumoniae* DNA cell equivalents (MHDCE) per milliliter.

Seventy six one-week-old pigs were distributed into 2 treatment groups. Litter mates were distributed between the treatment groups. Sixty of these animals (30 per treatment group) were from Ionia Feeder Pigs, Inc., Ionia, Iowa. Sixteen of the animals (8 per treatment group) were from the SPF swine operation at Solvay Animal Health, Inc., Charles City, Iowa. The first treatment group of pigs was vaccinated by intramuscular injection in the neck muscle behind the right ear at 1 week of age. The injections were repeated in the left side of the neck two weeks later. The second treatment group of animals was not vaccinated.

The Ionia pigs were weaned at 3 weeks of age and moved to an isolation room. The SPF pigs remained with the SPF herd until challenged.

The challenge material was produced and administered as previously described. At 1 month of age, 10 Ionia vaccinates, and 10 Ionia controls, along with 2 SPF vaccinates and 2 SPF controls were moved to an isolation room and challenged. At 2 months of age, eight of the Ionia vaccinates and eight controls, along with one SPF vaccinate and three SPF controls were moved to an isolation room and challenged. At 4 months of age, 8 of the Ionia vaccinates and 8 controls, along with 5 SPF vaccinates and 3 SPF controls were moved to an isolation room and challenged.

Three weeks after challenge, all pigs were euthanized and the percent lung lesion scores determined as previously described. Animals dying during the course of the study were not included in the analysis. A total of 8 non-vaccinates and 6 vaccinates died during the course of the study. These animals were generally poor performers or had severe intestinitis, pleuritis or pericarditis. Animals at necropsy with gross lung lesions of non-*M. hyopneumoniae* origin, i.e. surface fibrin, thoracic adhesions or hemorrhagic abscesses were not included in the analysis. A total of 1 non-vaccinated and 3 vaccinates exhibited such lesions.

Percent lung lesion scores were subjected to statistical analysis by a one-tailed Student T-test.

The lesion score results and the statistical analysis are presented in Table 4. There was an apparently age-related resistance to *M. hyopneumoniae* challenge that developed in all pigs, including non-vaccinates. The average percent lesion scores in both vaccinates and non-vaccinates decreased with the age of the animals at the time of challenge. It is not clear whether this increased resistance to challenge is an immunological or physiological phenomenon.

There was significant ($p<0.05$) protection afforded the vaccinates even at 4 months of age. The actual percent protection calculated as described previously decreased with the age of the animals. However, the 63 percent protection seen at 4 months of age still represents a substantial reduction in lesions.

The results of this test demonstrate that the *M. hyopneumoniae* bacterin is capable of inducing long lasting protection in pigs. Pigs vaccinated at 1 and 3 weeks of age are significantly protected even out to 4 months of age. The average market hog lives about 5–5.5 months. Vaccination with the *M. hyopneumoniae* bacterin should therefore provide protection during the crucial growing period. *M. hyopneumoniae* infections occurring after 4 months of age should not significantly impact performance.

TABLE 4

PERCENT LESION SCORES
AGE AT CHALLENGE (MONTHS)

| | 1 | | 2 | | 3 | |
|---|---|---|---|---|---|---|
| | VAC | CTL | VAC | CTL | VAC | CTL |
| 1 | 17.3 | 85.5 | 17.3 | 71.8 | 0.0 | 0.0 |
| 2 | 27.3 | 76.4 | 50.0 | 42.7 | 0.0 | 20.0 |
| 3 | 28.2 | 35.5 | 0.9 | 20.9 | 5.5 | 6.4 |
| 4 | 4.6 | 26.4 | 3.6 | 15.5 | 0.0 | 2.7 |
| 5 | 48.2 | 43.6 | 7.3 | 37.3 | 1.8 | 0.0 |
| 6 | 9.1 | 69.1 | 0.0 | 42.7 | 8.2 | 3.6 |
| 7 | 5.5 | 92.7 | 5.5 | 4.5 | 1.8 | 21.8 |
| 8 | | | 12.7 | 12.7 | 11.8 | 9.1 |
| 9 | | | 7.3 | 46.4 | 3.6 | 2.7 |
| 10 | | | | | 33.6 | 0.0 |
| 11 | | | | | 36.4 | 0.0 |
| 12 | | | | | | 1.8 |
| 13 | | | | | | 0.9 |
| AVG | 20.0 | 61.3 | 11.6 | 33.1 | 2.7 | 7.4 |
| STD | 14.6 | 24.1 | 14.5 | 18.0 | 3.5 | 7.7 |
| % PROTECT | 67.3% | | 64.9% | | 63.0% | |

STATISTICAL ANALYSIS (VAC VS. CTL. T-TEST, 1-TAILED)

| AGE AT CHALLENGE (MONTHS) | df | t | p |
|---|---|---|---|
| 1 | 12.0 | 3.59 | 0.0037* |
| 2 | 18.0 | 2.74 | 0.0135* |
| 4 | 20.0 | 1.81 | 0.0427* |

*SIGNIFICANT ($p < 0.05$)

EXAMPLE 4

In this example, *Mycoplasma hyopneumoniae* bacterins containing 7.0, 8.0, 9.0, 9.25 and 10.0 $\log_{10}$ *M. hyopneumoniae* DNA cell equivalents (MHDCE) per milliliter were evaluated in a minimum protective dose (MPD) study. The bacterins were administered as 2 milliliter intramuscular injections to pigs at 1 and 3 weeks of age. Significant ($p<0.05$) protection from challenge was elicited by bacterins containing $\geq 9.0$ $\log_{10}$ MHDCE per milliliter.

The animals used in this study were from Ionia Feeder Pigs, Ionia, Iowa. One hundred and twenty eight one-week-old pigs were placed in eight treatment groups of 16 pigs each. Litter mates were distributed among treatment groups. The pigs were ear tagged for identification. Three groups were not vaccinated. Each of the other five groups received one of the five bacterins. The vaccines were administered as 2 milliliter intramuscular (IM) injections in the neck muscle behind the right ear. The injection were repeated in the left side of the neck two weeks later.

The pigs were weaned at 3 weeks of age and moved to Solvay Animal Health, Inc. research facilities. The vaccinated pigs and two of the non-vaccinated groups of pigs were housed in two isolation rooms at Solvay. One of each of the nonvaccinate groups was placed in each of the two rooms. The third non-vaccinated group was housed separately to avoid exposure to extraneous *M. hyopneumoniae* challenge.

At four weeks of age, the vaccinates and two nonvaccinate groups (NV/CH) of animals were challenged with virulent *M. hyopneumoniae*. The third non-vaccinated group (NV/NC) which had been housed separately remained unchallenged.

Serum samples were obtained from each pig in the test at 1, 3, 4 and 7 weeks of age. Antibodies to *M. hyopneumoniae* were quantitated by ELISA as described in Example 2.

Three weeks after challenge, all pigs were euthanized and the percent lung lesion scores determined. Animals with gross lung lesions of non-*M. hyopneumoniae* origin, i.e. surface fibrin, thoracic adhesion or hemorrhagic abscesses were not included in the analysis. Animals dying during the course of the study were not included in the analysis.

Percent lung lesion scores were subjected to statistical analysis by a one-tailed Student T-test. The test revealed that the two non-vaccinated, challenged control groups were not significantly different from one another. The two groups were therefore combined prior to T-test analysis of the other treatment groups.

The ELISA results are presented in Table 5. At one week of age, the animals had measurable *M. hyopneumoniae* antibodies. Whole cell *M. hyopneumoniae* antigen is used in the ELISA. Therefore, it is difficult to eliminate the possibility that some of these maternally derived antibodies are directed against *Mycoplasma flocullare*. *M. hyopneumoniae* and *M. flocullare* share some antigens. Nevertheless, these maternal antibodies appear to rapidly disappear and by 3 weeks of age are uniformly low.

Those animals vaccinated with bacterins containing $\geq 9.0$ $\log_{10}$ MHDCE per milliliter seroconverted following the second vaccination at 3 weeks of age. An unexpected result was the increased titer in the non-vaccinated, non-challenged control group at 4 weeks of age prior to any challenge. The increase was, however, much less dramatic than in the vaccinated groups.

These results suggest that bacterins containing $\geq 9.0$ $\log_{10}$ MHDCE per milliliter effectively elicit *M. hyopneumoniae* circulating antibody titers.

The lesion score results and statistical analysis are presented in Table 6. In order to calculate the percent protection, the average percent lesion score of the non-vaccinated, non-challenged group was subtracted from the average percent lesion score of the other treatment groups. The resulting adjusted averages were then placed in the following formula:

$$\text{Percent Protection} = \frac{\left[\begin{array}{c}\text{Avg \% Lesion} \\ \text{Score of NV/CH} \\ \text{Group}\end{array} - \begin{array}{c}\text{Avg \% Lesion} \\ \text{Score of Test} \\ \text{Group}\end{array}\right]}{\text{Avg \% Lesion Score of NV/CH Group}} \times 100$$

It is clear that the percent protection elicited by vaccination increased as the dose increased. The T-test analysis revealed that significant ($p<0.05$) protection was achieved with bacterins containing $\geq 9.0$ $\log_{10}$ MHDCE per milliliter.

The treatment group receiving bacterin containing 7.0 $\log_{10}$ MHDCE per milliliter had an average percent lesion score higher than the nonvaccinated, challenged control group, suggesting that suboptimal doses may enhance lesion development following challenge.

These results support the conclusion that the minimum protective dose is about $2 \times 10^9$ MHDCE (2 milliliters of bacterin containing 9.0 $\log_{10}$ MHDCE per milliliter).

TABLE 5

ELISA READING AVERAGES

| TREATMENT GROUP | AGE AT BLEEDING (WEEKS) | | | |
|---|---|---|---|---|
| | 1 | 3 | 4 | 7 |
| NV/NC | 0.158 | ND* | 0.090 | 0.086 |
| NV/CH | 0.233 | 0.112 | 0.155 | 0.141 |
| 10^7 | 0.239 | 0.097 | 0.072 | 0.162 |
| 10^8 | 0.270 | 0.096 | 0.080 | 0.199 |
| 10^9 | 0.245 | 0.106 | 0.290 | 0.223 |
| 2.5 × 10^9 | 0.204 | 0.078 | 0.343 | 0.384 |
| 10^10 | 0.266 | 0.069 | 0.429 | 0.296 |

*NO SERUM SAMPLES AVAILABLE

TABLE 6

PERCENT LESIONS SCORES

| | NV/NC | NV/CH* | 10^7 | 10^8 | 10^9 | 2.5 × 10^9 | 10^10 |
|---|---|---|---|---|---|---|---|
| 1 | 0.0 | 11.8 | 6.4 | 10.0 | 0.0 | 3.6 | 0.0 |
| 2 | 0.9 | 9.1 | 18.1 | 9.1 | 5.5 | 6.4 | 2.7 |
| 3 | 0.0 | 10.9 | 19.1 | 7.2 | 10.0 | 32.7 | 0.9 |
| 4 | 0.0 | 16.4 | 10.0 | 4.5 | 0.9 | 2.7 | 0.9 |
| 5 | 11.8 | 2.7 | 2.7 | 0.9 | 14.5 | 6.4 | 7.2 |
| 6 | 0.0 | 0.9 | 6.4 | 24.7 | 3.6 | 1.8 | 0.0 |
| 7 | 3.6 | 0.0 | 71.8 | 18.2 | 13.6 | 0.0 | 5.5 |
| 8 | 0.0 | 16.4 | 0.0 | 10.0 | 37.3 | 2.7 | 7.3 |
| 9 | 0.0 | 18.2 | 5.5 | 5.5 | 17.3 | 6.4 | 8.2 |
| 10 | 0.0 | 39.1 | 75.5 | 17.3 | 23.6 | 12.7 | 8.2 |
| 11 | 0.0 | 34.5 | 15.5 | 13.6 | 5.5 | 19.1 | 29.1 |
| 12 | 1.8 | 60.9 | 31.8 | 22.7 | 1.8 | 27.3 | 2.7 |
| 13 | | 26.4 | 61.8 | 68.2 | 4.5 | 0.0 | 23.6 |
| 14 | | 43.6 | | 14.5 | 12.7 | 8.2 | 13.6 |
| 15 | | 47.3 | | 15.5 | 25.5 | 19.1 | 11.8 |
| 16 | | 10.9 | | | 10.9 | | |
| 17 | | 10.9 | | | | | |
| 18 | | 7.3 | | | | | |
| 19 | | 37.3 | | | | | |
| 20 | | 12.7 | | | | | |
| 21 | | 51.8 | | | | | |
| 22 | | 9.1 | | | | | |
| 23 | | 12.7 | | | | | |
| 24 | | 30.9 | | | | | |
| 25 | | 9.1 | | | | | |
| 26 | | 7.3 | | | | | |
| 27 | | 10.9 | | | | | |
| 28 | | 4.5 | | | | | |
| AVG | 1.5 | 19.8 | 25.0 | 16.1 | 11.7 | 9.9 | 8.1 |
| STD | 3.3 | 16.4 | 25.9 | 15.3 | 9.9 | 9.8 | 8.3 |
| % PROTECT | 100.0% | 0.0% | 0.0% | 20.2% | 44.3% | 54.1% | 63.9% |

*NV/CH ANIMALS 1–13 WERE IN ONE CHALLENGE ROOM, ANIMALS 14–28 WERE IN ANOTHER ROOM

STATISTICAL ANALYSIS (T-test, 1 TAILED))

| | | | df | t | p |
|---|---|---|---|---|---|
| NV/CH | VS | NV/CH | 38 | 3.73 | 0.0003* |
| | " | 10^7 | 39 | −0.76 | NEG |
| | " | 10^8 | 41 | 0.69 | 0.2471 |
| | " | 10^9 | 42 | 1.75 | 0.0437* |
| | " | 2.5 × 10^9 | 41 | 2.08 | 0.0219* |
| | " | 10^10 | 41 | 2.52 | 0.0079* |

*SIGNIFICANTLY DIFFERENT FROM THE NV/CH GROUP ($P < 0.05$)

EXAMPLE 5

A fluorometric assay for measuring *Mycoplasma hyopneumoniae* using the DNA binding dye Hoechst 33258 is described. The assay involves centrifugation of an *M. hyopneumoniae* culture to concentrate the cells, lysis of the cells in a detergent buffer and assay of the lysate. A minifluorometer (TKO-100, Hoefer Scientific) is used and a standard curve is established using purified DNA quantitated spectrophotometrically. Growth of an *M. hyopneumoniae* culture is monitored using the assay and the results compared with the traditional color changing unit (CCU) assay method.

One problem associated with *Mycoplasma hyopneumoniae* research is the difficulty of monitoring the growth of the organism. Because plating efficiency varies greatly at different stages of growth and because colonies are small and extremely slow growing, colony forming unit (CFU) assays are not practical. Traditionally *M. hyopneumoniae* cells have been enumerated by a color changing unit (CCU) assay. This assay involves making several dilutions of a culture into tubes of fresh media. The dilutions are then incubated for 14 days at 37° C. Tubes containing *Mycoplasma hyopneumoniae* exhibit an acidic pH shift. The titer of the original culture is expressed in terms of the highest dilution exhibiting growth. Because of the high experimental error of the CCU method, and the large number of replicate tubes required for the assay, a faster and more accurate test was needed.

Hoechst 33258 dye and the TKO 100 DNA miniflourometer were purchased from Hoefer Scientific Products. Herring sperm DNA was from Sigma Chemical Co. All other chemicals were reagent grade from Sigma Chemical Co.

*M. hyopneumoniae* isolate 1002 was grown in 200 ml cultures in shake flasks as described above in Example 1. Six flasks were inoculated and incubated in parallel. Samples were removed from each culture at 24 hour intervals to measure the pH and perform CCU and DNA assays. The pH values of each of the six cultures were averaged for each time point.

Color changing assays were performed as described above in Example 1. The CCU results from the six cultures were averaged for each time point.

For the DNA assay, four 1.5 ml aliquots of each culture were collected in microfuge tubes and centrifuged at 12,000×g for 10 minutes. The supernatants were completely drained off and the pellets resuspended in 120 µl of 10 mM Tris (pH 7.4) 150 mM, NaCl, 1 mM EDTA and 1% (w/v) sodium dodecyl sulfate (TNES). The resuspended pellets were vigorously vortexed for 10 seconds. Ten microliters of the resuspension was mixed in a glass cuvette with 2 ml of 0.04% (w/v) Hoechst dye in 10 mM Tris (pH 7.4), 150 mM, NaCl and 1 mM EDTA. The cuvette was placed in a TKO 100 DNA mini fluorometer which had previously been calibrated using Herring Sperm DNA standards diluted in TNES. Readings obtained or each of the four aliquots of each sampler were averaged and the results of the six cultures were also averaged.

The dynamic linear response range of the assay was approximately 20–2000 ng DNA per 10 ul test sample. This converted to an effective range of 0.16–16 ug DNA per milliliter of culture. The genome of *M. hyopneumoniae* is approximately $5\times10^8$ daltons (S. Razin, The Mycoplasmas. Microbiol. Rev. 42:414–470 (1978)). This corresponds to $8\times10^{-10}$ ug DNA per cell. The lower limit of the fluorometric assay is therefore (0.16 ug DNA per milliliter of culture)÷($8\times10^{-10}$ ug DNA per cell)=$2\times10^8$ cells per milliliter of culture. The upper limit is 100 times this value or $2\times10^{10}$ cells per milliliter.

This assay is an indirect measure of cell concentration, therefore the results are expressed as *M. hyopneumoniae* DNA cell equivalents or MHDCE per milliliter.

During the log phase of growth (24–72 hours) there is a good correlation between the MHDCE and CCU readings. The MHDCE are 4–5 times higher than the CCU values. It is generally felt that the CCU assay underestimates Mycoplasma concentrations. The DNA assay may therefore more accurately reflect the true number of *M. hyopneumoniae* cells. The CCU assay is inherently prone to experimental error. Large numbers of replicate tubes and a finer dilution series (twofold or fourfold) are required to improve the accuracy of the CCU assay. The DNA assay is less prone to experimental error. There is some error in the DNA assay due to the various sample manipulations and small volume measurements involved. However, this error is related to the skills of the operator performing the test. Most operators performthe DNA assay very well after a limited amount of training and experience.

The DNA assay measures all DNA whether in living or dead cells or free in solution. The CCU assay on the other hand measures only living cells. This explains why the MHDCE in a culture at 0 hours is slightly higher than at 24 hours. A substantial portion of the DNA measured at 0 hours is probably in dead and dying cells or cells that as a result of the serial transfer do not survive.

In stationary phase cultures (>72 hours) the CCU assay clearly reveals a loss of viable cells. *M. hyopneumoniae* is sensitive to acidic conditions and this death loss is probably pH related. The DNA assay is slower to respond presumably because the dead and dying cells still have DNA which is detected.

The CCU assay for quantitating *M. hyopneumoniae* suffers from several drawbacks. First, it probably underestimates the number of mycoplasma cells. Second, it is prone to experimental error. Large numbers of replicate tubes, expensive medium, and labor are required to reduce this error. Third, the assay requires at least 14 days to complete.

The DNA assay overcomes all of these problems. Mycoplasma cell estimates are higher than CCU estimates by 4–5 times and more accurately reflect the true cell count. When the proper equipment and training is provided the DNA assay is less prone to experimental error than the CCU assay. Finally, the DNA assay requires 15–30 minutes (more time is required if several samples are to be analyzed). This makes the DNA assay appropriate for real time monitoring of mycoplasma cultures. It should be remembered that the DNA assay measures all cells regardless of whether they are living or dead and regardless of their metabolic state.

The assay is therefore most informative during the log phase of the mycoplasma growth curve.

What is claimed is:

1. A bacterin comprising virulent *Mycoplasma hyopneumoniae* isolate 1002 (Strain P-5723-3/ ATCC Accession No. 55088), inactivated with binary ethyleneimine, in an amount not less than $10^9$ *Mycoplasma hyopneumoniae* DNA cell equivalents per milliliter of bacterin, a suitable physiologically acceptable carrier and an adjuvant.

2. The bacterin of claim 1, wherein the adjuvant comprises a polymer of acrylic acid.

3. The bacterin of claim 1, wherein the adjuvant is present in an amount of about 0.2% (w/v) of the bacterin.

4. A method of immunizing a swine against infection by *Mycoplasma hyopneumoniae* which comprises administering to the swine the bacterin of claim 1 so as to immunize the swine against *Mycoplasma hyopneumoniae* infection.

5. The method of claim 4, wherein the bacterin is administered intramuscularly.

6. The method of claim 4, wherein about 2 milliliters of the bacterin are administered twice to the swine.

7. The method of claim 6, wherein the two administrations of the bacterin occur first at about one week and then at about three weeks after the birth of the swine.

* * * * *